United States Patent

Hering

Patent Number: 6,146,881
Date of Patent: Nov. 14, 2000

[54] DEVICE AND METHOD FOR HANDLING OBJECTS IN A LIQUID BATH

[75] Inventor: Steffen Hering, Blasius Hueber Strasse 15, A-6020 Innsbruck, Austria

[73] Assignee: Steffen Hering, Innsbruck, Austria

[21] Appl. No.: 09/160,025

[22] Filed: Sep. 24, 1998

[30] Foreign Application Priority Data

Sep. 24, 1997 [DE] Germany .............................. 197 42 163

[51] Int. Cl.[7] .................................................. A01N 1/00
[52] U.S. Cl. ..................................... 435/284.1; 435/289.1; 422/100; 422/102; 422/104
[58] Field of Search ................. 435/288.7, 284.1, 435/289.1; 422/100, 102, 104

[56] References Cited

FOREIGN PATENT DOCUMENTS

| 3223589 | 12/1983 | Germany . |
|---|---|---|
| 3321239 | 5/1985 | Germany . |
| 2530697 | 7/1986 | Germany . |
| 2928790 | 12/1987 | Germany . |
| 4305405 | 5/1994 | Germany . |
| 4321062 | 1/1995 | Germany . |

*Primary Examiner*—David A. Redding
*Attorney, Agent, or Firm*—Robert A. Koons, Jr.; Kenneth Crimaldi; Pepper Hamilton LLP

[57] ABSTRACT

In an apparatus used for perfusion-treating objects within a defined treatment area of a liquid bath, the apparatus having a ring having a lower edge which is sealingly placeable on the bottom of the liquid bath and an interior for connection to a liquid conveying device. The ring includes a holding member for receiving an inlet member of the liquid conveying device, or a wall having at least one wall chamber which communicates with the holding member on the ring and with the interior of the ring.

28 Claims, 8 Drawing Sheets

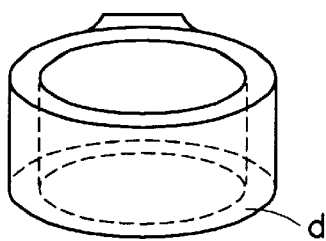
Fig. 1a0
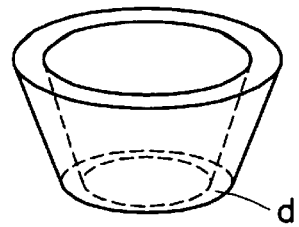
Fig. 1a1
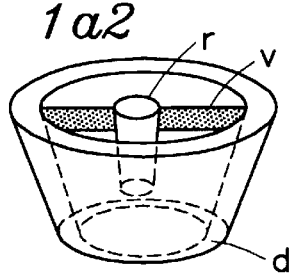
Fig. 1a2
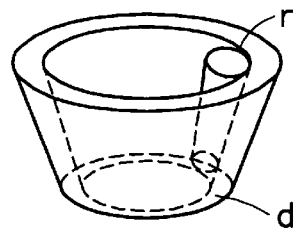
Fig. 1a3
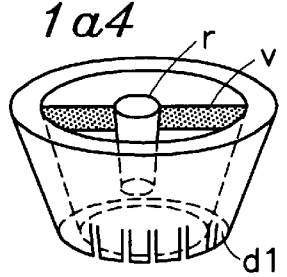
Fig. 1a4
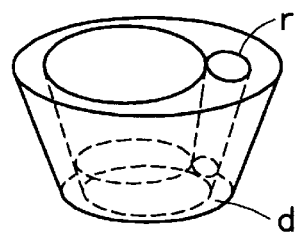
Fig. 1a5
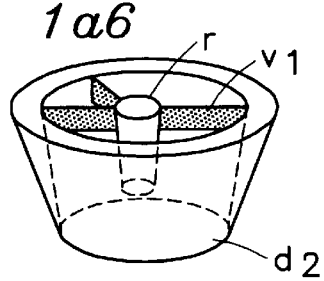
Fig. 1a6
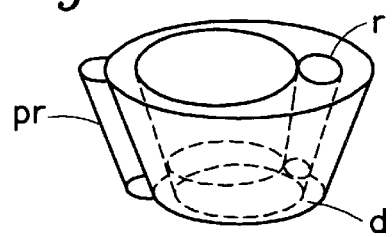
Fig. 1a7
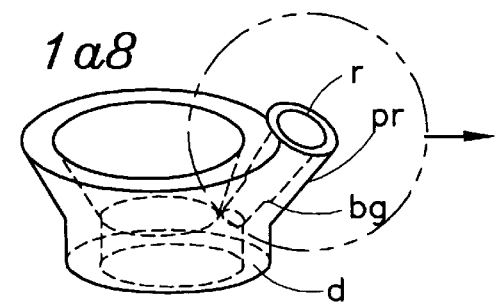
Fig. 1a8
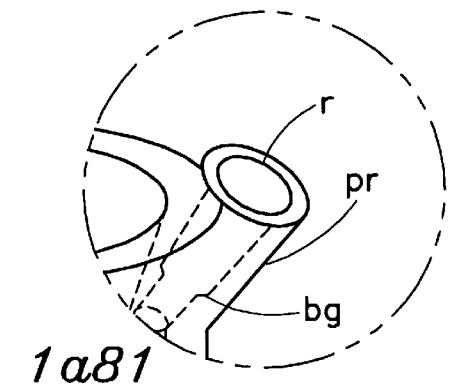
Fig. 1a81

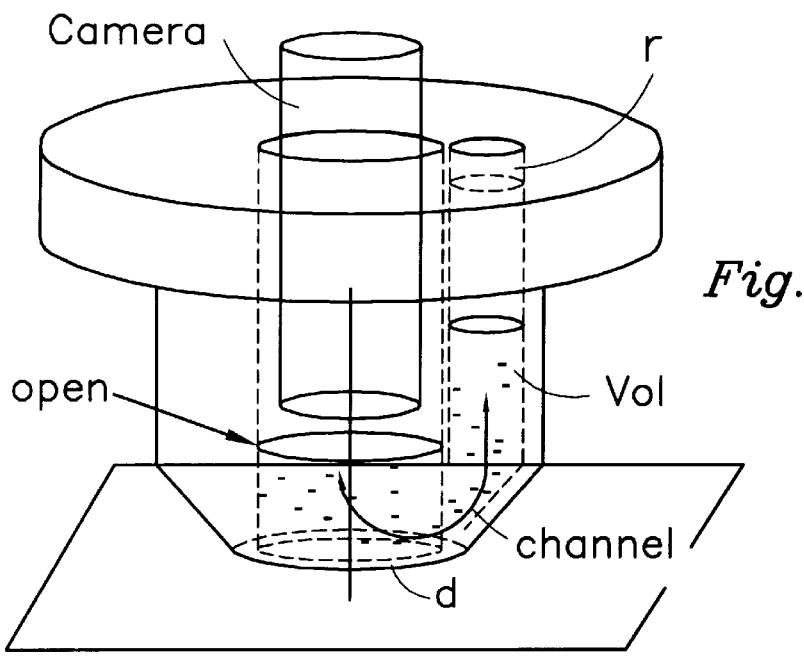
*Fig. 1a9*
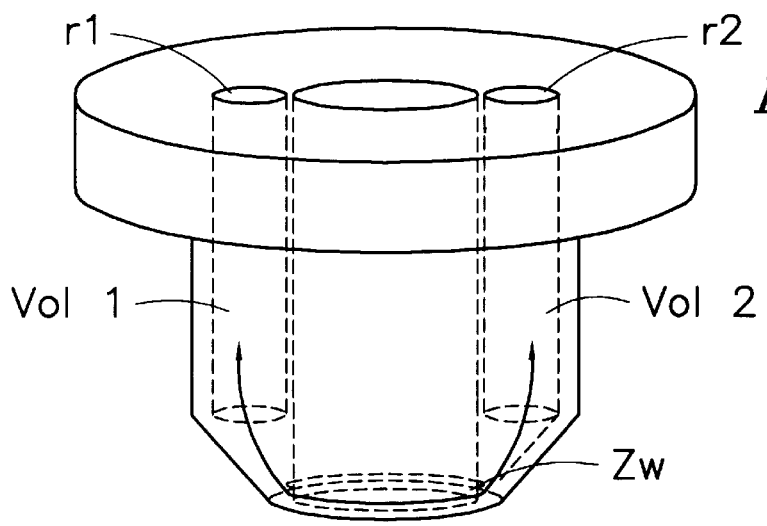
*Fig. 1a10*
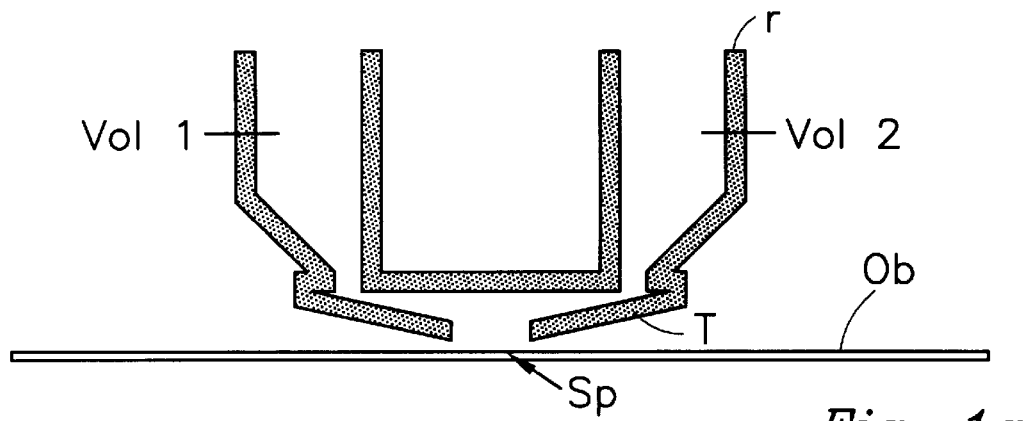
*Fig. 1a11*

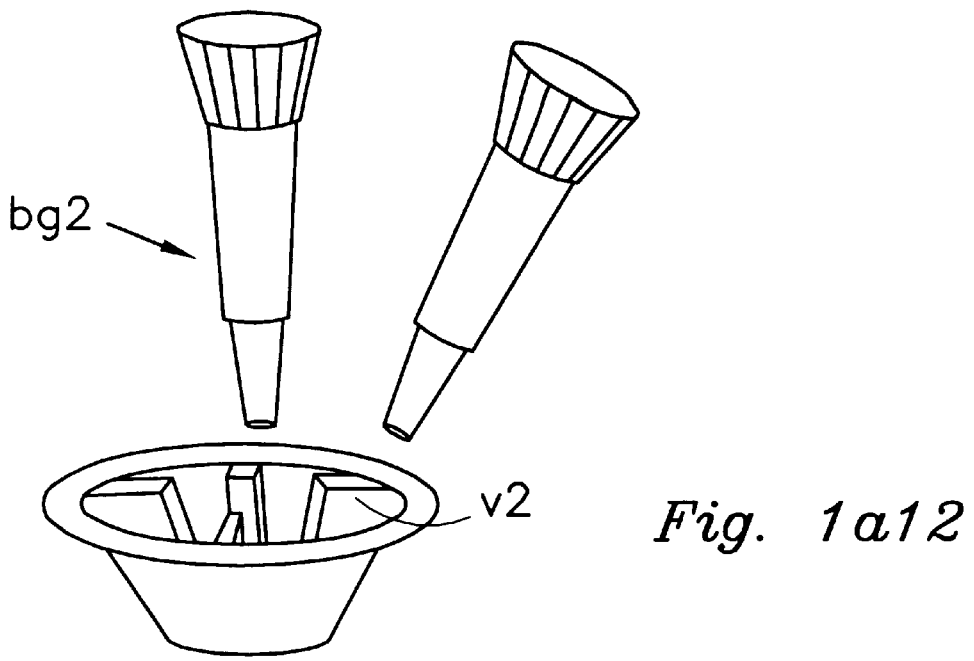
Fig. 1a12
Fig. 1a13
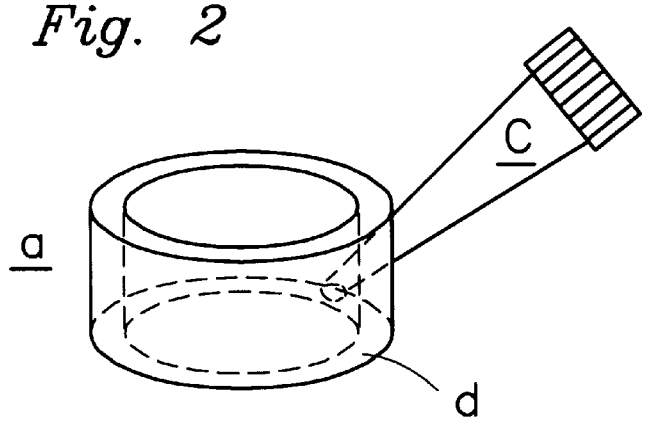
Fig. 2

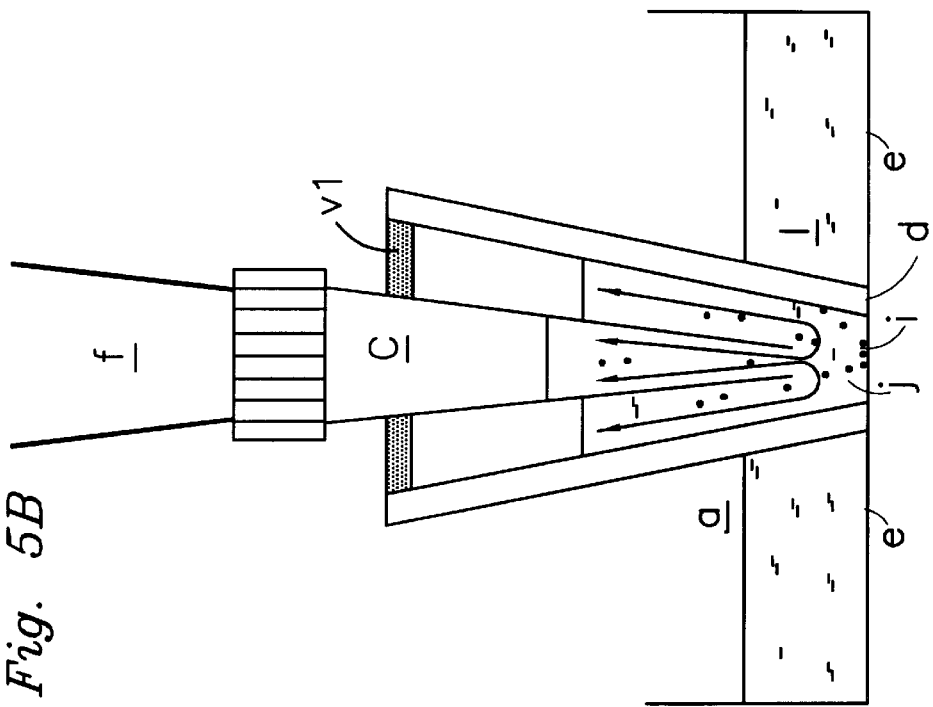
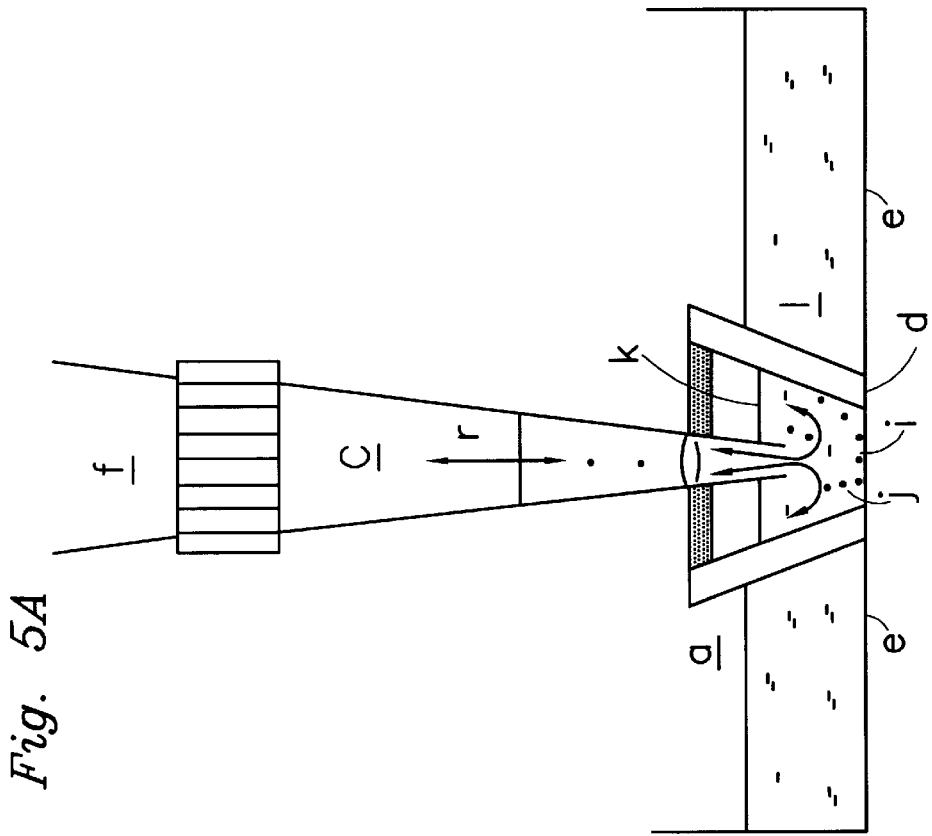

600
DEVICE AND METHOD FOR HANDLING OBJECTS IN A LIQUID BATH

FIELD OF THE INVENTION

The present invention relates to devices for handling or treating objects in a liquid bath, in particular to a device used for perfusion treatment within a defined treatment area of a liquid bath, and to a method for using said device.

BACKGROUND OF THE INVENTION

DE-OS 43 05 405 discloses an apparatus for analyzing an object immersed in a perfusion liquid covering a substrate. The apparatus contains a perfusion chamber which is configured to receive a perfusion liquid via an inlet tank and to draw off the perfusion liquid through an outlet. The inlet of the inlet tank is designed such that an analyzing device can also be introduced into the interior of the perfusion chamber. This known apparatus has the drawback that the perfusion liquid is introduced into the chamber via a funnel-shaped inlet opening and is only drawn off in one direction. Therefore, the chamber is not suited for repeated flushing operations in two directions (forward and backward), nor for a subsequent removal of the objects. Moreover, the chamber is also not suited as a single-use article for sterile operations, e.g. with cell cultures, because of the complex and time consuming drilling and milling associated with the manufacturing method used for the chamber.

An improvement over the known perfusion chambers is described in DE-OS 43 21 062. For perfusion treatment, in particular of biological objects, the objects are exposed to a directed liquid flow having a defined area of operation. The liquid flow is formed by two suitably combined pipette tip members or an applicator member shown for illustrative purposes in FIG. 7. The applicator member is an annular component 70 having a specifically designed pipette tip member 71 which differs from conventional pipette tip members in that it has a curvature and is directly connected to the wall of annular component 70, thereby forming a perfusion liquid inlet. A liquid conveying device 72 is removably attached to the pipette tip member 71. The applicator member can be attached with a lower sealing edge onto a substrate 74 to enclose the substrate 74 to be treated. The perfusion treatment involves, in particular, the alternate discharge and drawing of perfusion liquid through the pipette tip member.

The apparatuses described in DE-OS 43 21 062 have the drawback of requiring manipulation of conventional pipette tip members. Conventional pipette tip members (i.e. easily manufactured members that taper toward the tip without any curvature and are regularly used for metering and proportioning liquids) must be used either in the combination (i.e., two pipette tips are positioned together or even attached and operated by two liquid conveying devices) or a special applicator member has to be manufactured in the case where the pipette tip member is connected to an annular component.

The applicator member described in DE-OS 43 21 062 and shown in FIG. 7 has the following further drawbacks. The applicator member has an asymmetric shape with curved portions that do not permit any simple injection molding manufacturing processes to be used. Because of the nature of the connection between the annular component 70 and the pipette tip member 71 this device is not suitable for precise handling of liquids and suspensions. Specifically, adhesive forces at the inner and outer surface of the annular ring create an undesired "dead" volume of perfusion liquid (perfusion liquid that adheres to the annular ring and therefore is not utilized in the treatment process). The dead volume practically excludes the handling of precise liquid volumes with the device shown in FIG. 7. Further, the undesired dead volume creates cleaning problems.

Since conventional pipette tip members which are suitable for precise liquid handling and attachable to a liquid conveying device (such as "Costar," "Eppendorf" (Germany) and "Gilson" (France) pipettes) cannot be used in the DE-OS 4321 062 device, the applicator member must be adapted to the respective liquid conveying device 72. Hence, a large-scale production of universally usable applicator members is not possible. The structure of the known applicator member leads to mechanical instability due to the lever effect of the pipette tip member 71 on the curved portion, which is detrimental to the sealing of the lower edge of the applicator member 70 relative to the substrate 73 and to its use in automated systems. The asymmetric form of the applicator member is in general difficult to handle, because a mounting of the applicator member on the liquid conveying device always necessitates alignment of the two members and is not suitable for precise handling of liquid volumes.

Due to the drawbacks described above, known applicator members have so far only been used in laboratories. However, rapid progress in analytic methods for genetic engineering have created great interest in perfusion devices that can be mass-produced, and that can be reliably and automatically operated. The above-mentioned drawbacks are found not only in perfusion devices, but generally in all devices used for treating objects within a defined treatment area in a liquid bath (e.g. perfused, diluted, flushed, partially dissolved, mixed, removed or the like), as well as in apparatuses used for mixing liquids.

SUMMARY OF THE INVENTION

It is an object of the present invention to provide an improved treatment device which makes it possible to overcome said drawbacks. It is also an object of the present invention to provide novel methods for object or liquid treatment using the device.

In contrast to known applicator members, the invention utilizes a ring (also called delimiting ring, cloning ring, perfusion cup or perfusion ring) comprising a holding member which forms a frictional or non-positive receiving portion for a tip-like inlet member of a liquid conveying device. The invention enables treatment of an object in a defined treatment area within a liquid bath, for instance, on a substrate. The holding member is provided for inserting or attaching any desired tip-like inlet members in a non-positive manner. Tip-like inlet members are all components of liquid conveying device which form a tubular or capillary, optionally conically tapering feed line with a typical end diameter which is smaller than (in particular smaller than half of) the upper edge diameter of the interior formed by the ring. The holding member is capable of receiving a syringe or pipette tip, but may also be a projecting attachment via which the inlet member can be attached.

The liquid conveying device is either designed for the discharge of liquid or for the generation of liquid movement in a perfusion ring by the exertion of pressure. In one embodiment of the invention, the perfusion ring is made of a soft elastic or flexible material (e.g. silicone or rubber) which in any desired wall portion can be pierced by the tip of the inlet member from the outside to the interior of the ring. In such a case the holding member is formed at the piercing point at which a non-positive seal is formed between the ring material and the inlet member.

In another embodiment, the holding member is provided in the interior of the perfusion ring. In this embodiment, the holding member can comprise an annular receiving portion which is optionally connected via bridge members to the wall of the perfusion ring. The annular receiving section is, for example, an elongated insertion section having a conical cross-section which tapers towards the bottom of the perfusion ring. The receiving area may be provided in axial symmetry in the center of the perfusion ring or in an eccentric manner on the wall of the perfusion ring. When the receiving area is in the center of the perfusion ring, additional connection members (bridge members) are provided for stabilizing the receiving portion relative to the perfusion ring. The annular receiving section is made from an elastic or non-elastic material. In the case of an elastic receiving portion, the inner diameter of the elastic receiving section is slightly smaller than the pipette tips that are engaged. However, since the material is elastic, inlet members (in particular pipette tips) with greatly varying diameters can be inserted in a non-positive manner. In the case of a non-elastic receiving portion, the receiving portion has a snug fit with the pipette tip (e.g. a conical fit).

In still another embodiment, the holding member is embedded in the wall. To this end, the wall is provided with a funnel-shaped enlargement on the outside of the ring, which simultaneously forms a profile on the outside of the ring. The wall may also be provided with at least one inner wall chamber which communicates with the interior of the ring.

In yet another embodiment, the receiving portion of the perfusion ring (perfusion cup) is provided with an inner stop which ensures that the pipette tip can only be inserted up to a certain point into the receiving device. The stop is a limiting element or boundary which defines the insertion depth for the pipette tip member.

According to the invention it is possible to attach the perfusion ring detachably or fixedly to the inlet member of the liquid conveying device. When detachable, the perfusion ring can be received in a particularly advantageous manner with the inlet member and it is possible to disengage the perfusion ring from the inlet member manner after the treatment has concluded.

The invention enables precise liquid handling. According to the invention it is possible to draw a defined volume (i.e. by means of conventional air displacement pipettes) in a conventional pipette tip member and, thereafter, attach the pipette tip to the perfusion ring. This two step procedure (first handling of a precise volume with a conventional tip and thereafter connection of the filled tip to the ring) enables precise volume control of the perfusion treatment.

According to the method of the invention, a perfusion ring is attached to a pipette-like tip of the liquid conveying device and is moved together with said device to a liquid bath including at least one object to be treated. After the perfusion ring has sealingly been mounted by means of the inlet member onto the substrate bottom of the liquid bath, treatment is carried out by operating the liquid conveying device. Subsequently, the perfusion ring is again moved with the aid of the inlet member to a storing device. According to a preferred embodiment of the invention, the treatment method is automated in such a manner that the inlet member with the perfusion ring is controlled by a manipulation device. The manipulation device is connected to an image processing device which enables the inlet member with the perfusion ring to move to a predetermined position on the liquid bath.

The objects treated according to the invention may be any desired synthetic or biological objects, in particular biological cells, cell groups, cell components, viruses, or the like, but also other particles, such as macromolecules or the like.

BRIEF DESCRIPTION OF THE DRAWINGS

Further details and advantages of the present invention will now be described with reference to the attached drawings, in which:

FIGS. 1a0–a13 are schematic perspective views of perfusion rings according various embodiments of the invention;

FIG. 2 is a schematic phantom view of a perfusion ring in accordance with the invention with inserted inlet member;

FIGS. 5A, 5B are a further sectional views for illustrating the use of a treatment device in accordance with the invention;

DETAILED DESCRIPTION OF THE INVENTION

FIG. 1 shows various embodiments of inventive delimitation or perfusion rings, with illustrations $a0$ and $a1$ representing two preferred basic forms that may each be designed in accordance with the variants according to $a2$ to $a11$ or according to FIG. 2. According to FIG. 1$a0$ the ring has the shape of a hollow cylindrical or tubular section. The bottom surface, which when used forms contact surface d, is a flat sectional area. The contact surface d is configured such that a liquid-tight contact area is formed when the contact surface firmly rests on a substrate surface. According to FIG. 1$a1$ there is provided a tapering perfusion ring which has the shape of a hollow truncated cone. The contact surface d is again configured to form a tight contact with a substrate surface.

In all of the embodiments, the contact surface has a sealing effect due to the fact that the respective ring is made of a soft elastic (flexible) material and is coated on its bottom side with a soft elastic seal.

In contrast to FIGS. 1$a0$ and 1$a1$, the contact surface d can form an angle $\neq 90°$ relative to the symmetrical axis of the cylinder or the truncated cone. In the embodiment of FIG. 1$a1$, the flat contact surface d may also be provided at the larger end of the truncated cone. In case the perfusion ring has a symmetrical structure relative to a center axis, there will be advantages regarding ring production and handling. A pipette tip is preferably inserted into the perfusion ring in vertical direction or obliquely from above into the area of the upper edge of the perfusion ring wall. Oblique insertion from above means that the pipette tip is inclined relative to the vertical line and is inserted into an upper ring portion such that an insertion force is substantially directed towards the lower contact surface, with a torque being created relative to the lower edge, which guarantees stable placing of the contact surface.

According to one of the above-mentioned embodiments of the invention, a holding region is provided for an inlet member of a liquid conveying device as part of the ring wall consisting of a soft elastic material. This embodiment will be explained in detail further below with reference to FIG. 2.

According to another of the above-mentioned embodiments, an annular receiving portion r is provided in the interior of the perfusion ring and being optionally connected via at least one connection member v, v1 with the annular wall, as is shown in FIGS. 1a2, 1a4 and 1a6. Apart from the hollow cylindrical or cone-shaped form, the annular receiving portion r may have any cross-sectional shape (square, polygon or the like). According to the invention a liquid-tight connection need not exist between the receiving portion and the inlet member received in the operative state.

Figure 6:
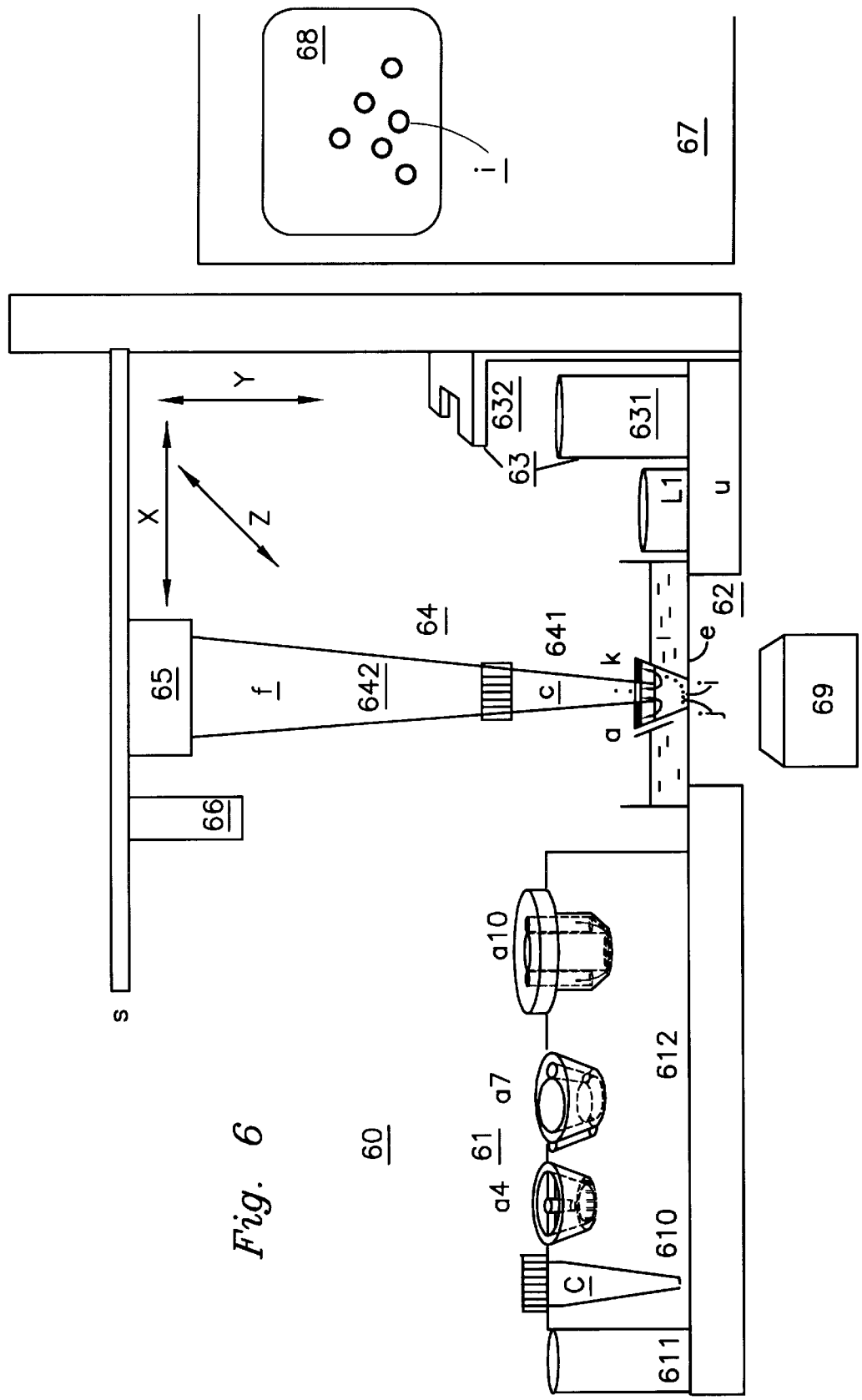
FIG. 6 is a schematic representation for illustrating a method in accordance with the invention.

According to FIG. 1a2 the annular receiving portion r is arranged in axial symmetry and configured such that the tip of the inlet member in the operative position is oriented in vertical direction above a substrate. Especially with respect to automated techniques, a vertical insertion into the center of the symmetrical ring is particularly advantageous because of an increased mechanical stability. According to FIG. 1a3 the annular receiving portion r is directly mounted on the wall of the perfusion ring. FIGS. 1a4 and 1a6 show modifications of the contact surface d1 and d2, respectively.

According to FIG. 1a4, the lower edge of the perfusion ring is provided with incisions which guarantee additional sealing upon contact with a substrate and a simplified mechanical removal of the ring from the substrate. The contact surface d2 according to FIG. 1a6 has a ring width smaller than the wall thickness of the ring (tapered bottom edge of the ring). It is in general possible to compose an inventive perfusion ring of several materials, with at least the respective receiving portion and the contact surface being made of an elastic material.

Figure 7:
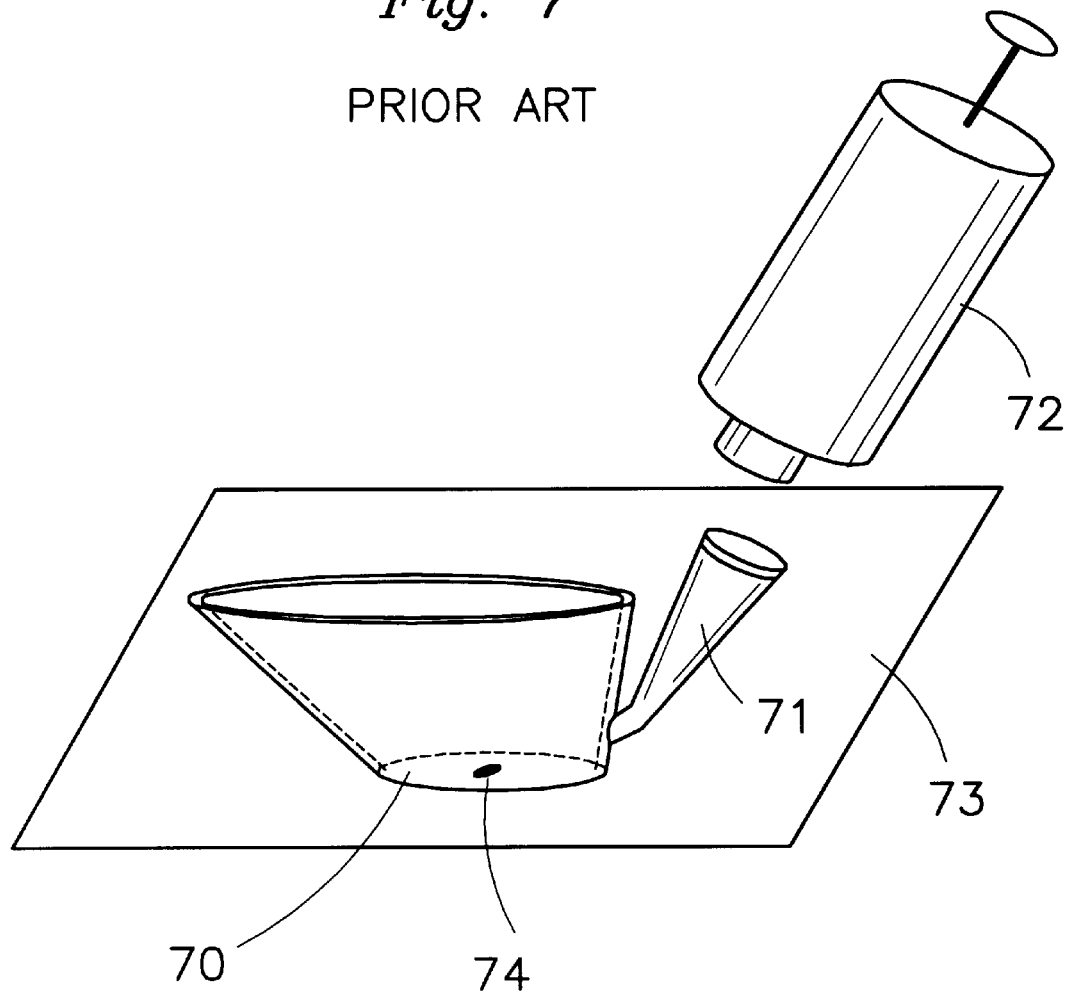
FIG. 7 is a perspective view showing a conventional applicator member (prior art).

FIGS. 1a5 and 1a7 are modifications of an inventive perfusion ring which are characterized by an asymmetrical structure. Irrespective of the advantages of the above-described symmetrical structure, asymmetrical perfusion rings are also suited for automated processes. According to FIG. 1a5 the annular receiving portion r is embedded in the wall of the perfusion ring. To this end, as shown in FIG. 1a5, the wall may have a thickness varying across the ring circumference, with the receiving portion r being positioned in an area of increased wall thickness. The thickness of the annular wall also varies in axial direction. This means that the wall thickness in the area of the contact surface d which is the lower one in the operative state is smaller than the wall thickness at the opposite (upper) side of the ring. As shown in FIG. 1a5, the transition between the two wall thicknesses is preferably stepped, resulting at the bottom side of the perfusion ring in an enlarged portion of the ring interior into which the inlet member, which is received by the receiving portion, projects. The contact surface (d2) can also be sharpened, as shown in FIG. 1a6(d2). In FIG. 1a5, this stepping is shown in broken line. The height of the stepped portion relative to the contact surface d is chosen such that the end of the inlet member which projects through the receiving portion r does not strike the substrate bottom.

In the embodiment shown in FIG. 1a7, the outer wall of the perfusion ring has provided thereon a thickened portion pr which is designed to position the perfusion ring in a holding device, for example in the preparation station 61 shown in FIG. 6 (see below). Instead of the thickened portion pr, there may be another profiled exterior shape of the ring wall. This is of particular advantage to a reproducible positioning of the perfusion rings on a perfusion ring supplier 612 (see FIG. 6).

As shown in FIG. 1, it is possible to introduce the inlet member (pipette tip) in vertical direction from above (FIGS. 1a2, 1a4, and a6) or at an inclined position relative to the vertical insertion (FIGS. 1a5, 1a7) into the perfusion ring.

In the constructions shown in FIGS. 1a8 and 1a81, which are also asymmetrical, the receiving portion r and the lateral thickened portion pr are made integral. This means that the receiving portion r is formed in the thickened portion pr. A pipette tip member or the like can be inserted from the top side of the ring into the receiving portion r, so that the member will terminate through an inner channel in the interior of the perfusion ring. The inner channel may have a stop bg which forms a boundary when the pipette tip member is introduced.

The constructional shape 1a9 represents a particularly important embodiment of inventive perfusion rings in which the receiving portion r is laterally enlarged in the wall of the perfusion ring to form a volume Vol (wall chamber). In connecting r to a fluid conveying device, it is first possible through a drawing action to receive a liquid (e.g. a reaction component for a chemical reaction or an enzyme solution for the treatment of cells that are positioned on a surface) in said volume Vol. When the ring is subsequently positioned on a surface (by applying a small pressure), a reciprocating or pendulum-like perfusion of the surface as defined by the perfusion cup can be achieved for the desired treatment, e.g. of cells, on the surface by ejecting and drawing in the liquid amount through a channel or nozzle connection with the interior.

The constructional shapes 1a10, 1a11 are further embodiments of the inventive perfusion rings in which two receiving portions r1, r2 and two volumes Vol 1, Vol 2 are positioned in the wall of the ring. Perfusion is carried out in these embodiments in the same way as in the constructional design a9, and the liquid amount can here additionally escape into the second volume. At the second receiving portion r2 (1a10) a negative pressure (suction) can be applied at the same time (synchronous with the pressure applied), and the liquid level in the cup can be kept constant (by synchronously operating a suction and pressure device).

In the perfusion rings, a continuous opening can be positioned in the center of the rings. A camera, an optical cable or another optical device can be introduced into such an opening. When this optical device is positively secured to the wall of the ring, the perfusion volume is closed.

To rule out a situation where the cells to be removed or other objects are contaminated by the optical device and/or in order to flatten the perfusion volume in the interior so as to increase the shear forces perfusing through the liquid flow, the opening in the center may also be defined by a partition wall (Zw, see a10). A further advantage of such a design is that the forces acting on the substrate surface can be compensated by pressing the lower edge (d) onto the surface. Furthermore, the soft material of the ring can be compressed and the perfused volume on the surface (Ob) can be reduced. The partition wall can also be designed as an optical imaging device (e.g., in the form of a lens).

The perfusion cup of the invention can generally consist of one or more parts. The lower part (T) of the cup which rests on the surface (Ob) comprising objects (or defining a reaction volume) is designed such that it consists of an attachment cap made of a soft, sealing material or also of a flexible material (such as PTFE). In the last-mentioned case, the sealing effect is achieved by applying pressure across a tapering edge (Sp) onto the surface (Ob) (example: sectional view a11). The attachment cap T can be attached from below to a corresponding receiving portion on ring r and can be designed to vary the perfusion volume in the interior of the ring and/or the defined portion on the surface. There may be provided a plurality of attachment caps T having different lower attachment diameters which within the scope of the method described hereinbelow are selectively attached to the perfusion ring.

The embodiments a12 and a13 of FIG. 1 illustrate a further modification of the holding member. On the inner wall of the rings, at least three ribs, bars or bridges are arranged forming compartments and a central receiving portion for the tip-like inlet member of a liquid conveying device projecting from above into the interior of the ring. At least one rib has a stop or limiting element bg1 for restricting the downward movement of the inlet member. Additionally, the inlet member can carry a restricting piece or attachment bg2. These elements allow both a perpendicular and an inclined insertion of the inlet member.

All of the embodiments have in common that the respective holding member for the non-positive reception of a tip-like inlet member is arranged on the upper edge or disposed such that it is adjacent to said edge (at some distance from the lower edge) or is connected to said edge via connection members. Such a geometrical shape provides two advantages of the present invention. First, an inlet member of a liquid conveying device is insertable in a stable manner. During insertion a torque is formed for stabilizing the mounting or placing of the contact surface. A destabilizing torque that could tilt the perfusion ring is eliminated. Secondly, when the inlet member is engaged the treating liquid can be introduced such that the treating liquid flows downwardly onto the substrate, whereby the perfusing shear forces are increased. As a result, the flow rate component which is oriented in vertical direction relative to the substrate surface is greater than the flow rate component which is oriented in parallel with the substrate surface.

The embodiments comprising wall chambers (a9, a10, a11) have the additional advantage that these are suited for an immediate and direct connection via a connection member to the liquid conveying device or a pressure device. A pipette tip need not additionally be used as an inlet member because the ring itself serves as a liquid receiving means.

All figures show perfusion rings with open top sides allowing a pressure compensation during the operation. According to a modification which is possible with each of the illustrated embodiments, the perfusion ring has a closed side opposite to the contact surface side. The wall material of the ring forms a lid or cover. In operation, the ring on its top side is closed forming a chamber with a certain amount of air above the liquid bath. Accordingly, the air in the chamber is compressed when liquid is discharged therein. The increased pressure supports following suction steps. For these embodiments, the receiving portion for the tip-like inlet member should have an air-tight seal.

The dimensions of the perfusion rings can be varied depending upon the demands of the application. As an example, cell clones have a diameter of about 1 mm. Accordingly, typical dimensions are as follows. The inner diameter of the contact surface preferably is in the range of 2 to 5 mm, e.g. 3 mm. Larger diameters up to 10 mm are also possible. The diameter of the top side of the rings depends on the constructional shape. With the cylindrical shape according to FIG. 1(a0), the upper diameter is identical to the diameter of the contact surface. With conical shapes, the upper diameter is greater (e.g. in the range of 4 to 8 mm). A typical dimension for the height of the ring is in the range of 3 to 4 mm up to several centimeters.

FIG. 2 shows an example of the above-mentioned first embodiment in which a perfusion ring is formed by a simple cylindrical or conical ring a made of a flexible, soft elastic material. The inlet member of the liquid conveying device is formed by a needle or pipette tip member c. The material of the ring a is of such a type that the tip c can be inserted into the ring wall next to the upper edge by applying a shear force which is axial relative to the tip axis. An additional advantage of such a material selection is that the contact surface d is soft and elastic and a self-adjustment or autoadaption of the contact surface is thereby achieved relative to a substrate surface.

Figure 3:
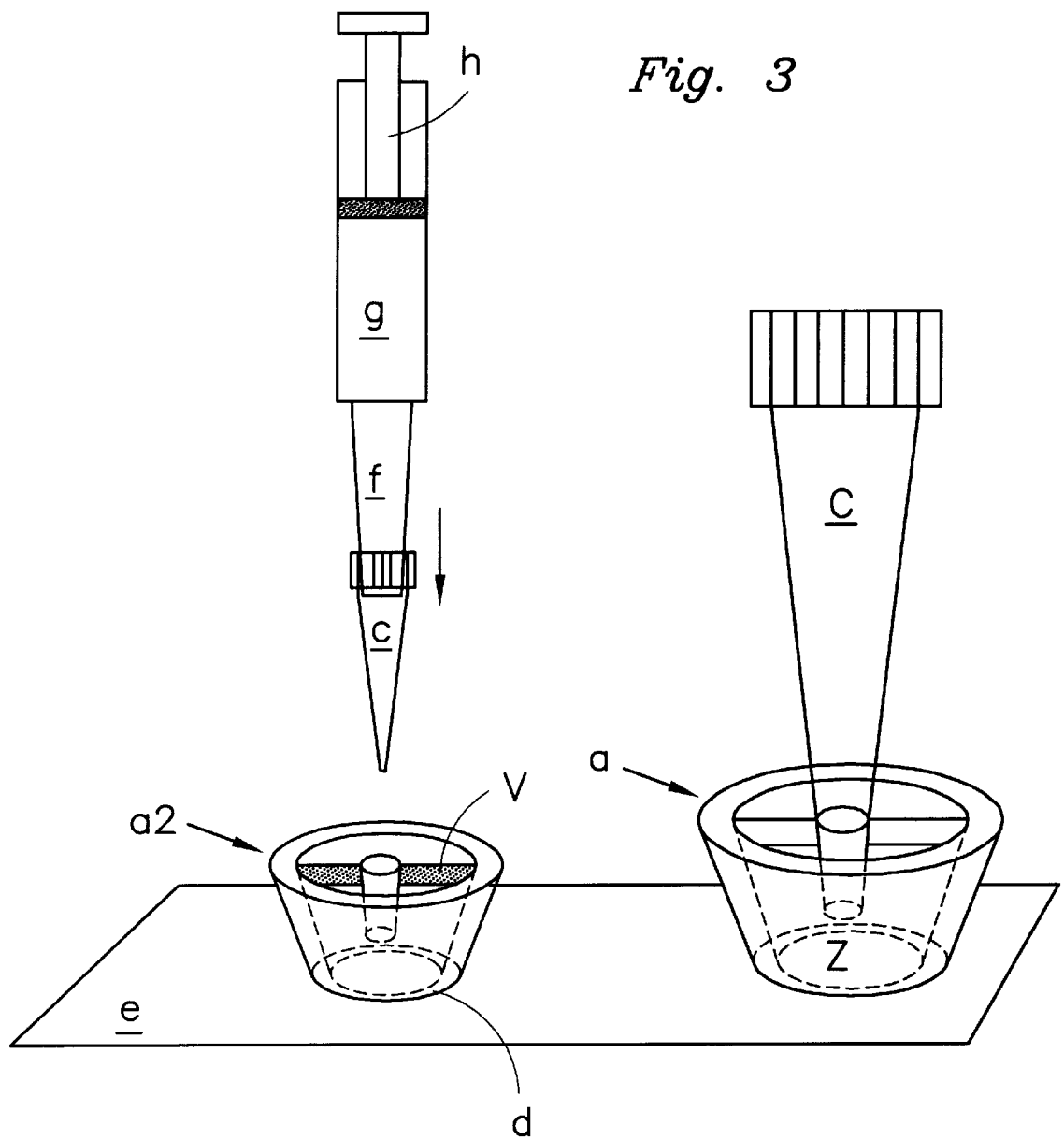
FIG. 3 illustrates the receiving portion of a perfusion ring in accordance with the invention with the inlet member of a liquid conveying device and is a schematic perspective view of a pipette tip of the invention with fixedly mounted perfusion ring.
Figure 4:
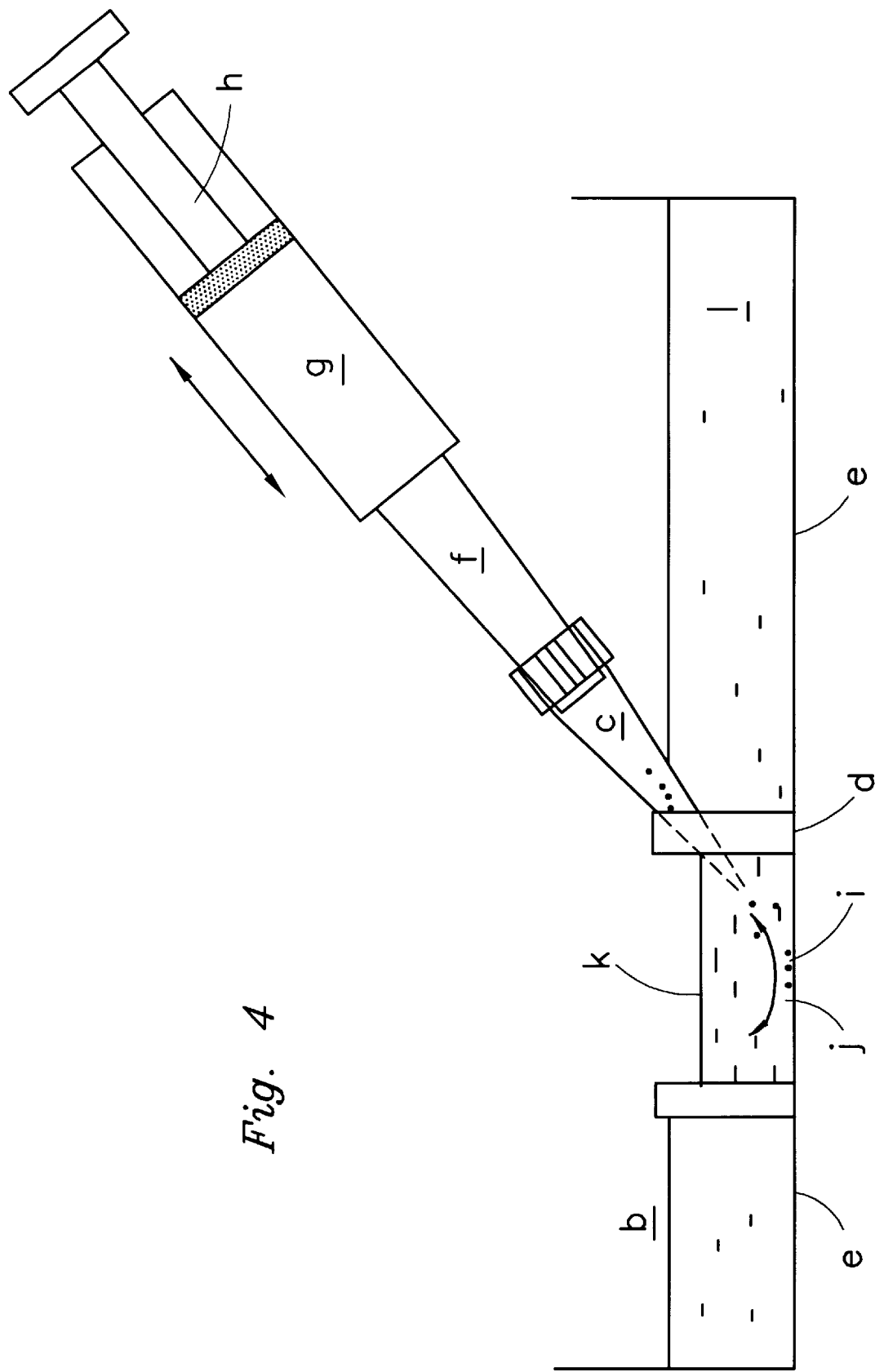
FIG. 4 is a sectional view for illustrating the use of a treatment device in accordance with the invention.

FIG. 3 shows the cooperation of inventive perfusion rings with the inlet member of a liquid conveying device. A perfusion ring which rests on a support e (see FIG. 1a2) is received by the inlet member through a downward movement of the liquid conveying device. The liquid conveying device, for instance, a pipette plunger (other proportioning or dosing devices can be used) comprising plunger g and plunger rod h is connected via a connection member f to a pipette tip c that forms the inlet member. Following a downward movement in the direction of the arrow, the pipette tip c is positioned in the perfusion ring in a non-positively inserted state. In this state the perfusion ring can be moved with the pipette tip c or can be used for a desired object treatment.

The right part of FIG. 3 shows a special embodiment of the invention in which a pipette tip c (mounting tip) is fixedly connected to a perfusion ring a. This design can be modified according to the ring shapes of FIGS. 1, 2.

An advantage of the symmetrical design with vertical pipette tip is that a liquid flow can be passed with the pipette tip c into the inner volume of the ring a in such a manner that the liquid impinges on a substrate surface at an angle of 90° or, in the embodiments a3, a5, a7, a8 and a9 according to FIG. 1, at an angle smaller than 90°. Thus, an additional flushing pressure can be exerted with the discharged perfusion liquid, the additional pressure enhancing the efficiency of the object treating process in comparison with conventional perfusion chambers. Efficiency is additionally enhanced in cases where the pipette tip c is nozzle-shaped.

The use of an device of the invention according to FIG. 2 is shown in FIG. 4. A container (e.g. dish for cell cultures) contains a liquid bath 1 in which objects i to be treated are positioned. The bottom of the container forms a substrate e which has placed thereon the perfusion ring b whereby the objects i are separated from the remaining liquid bath. The contact surface d forms a liquid-tight contact portion with the substrate e. A treatment liquid can be supplied to the interior of the perfusion ring b with the liquid conveying device comprising pipette tip c, connection member f, plunger g and plunger rod h. It is possible to remove excess parts of the liquid bath 1 from the defined volume beforehand to prevent an overflow of the liquid level k. The objects can be exposed to a perfused liquid flow (bent double-headed arrow) with the treatment liquid and/or parts of the liquid bath by alternately operating the plunger rod h of the plunger g of the liquid conveying device (straight double-headed arrow). It is also possible to draw objects into the liquid conveying device for treatment in plunger g and, subsequently, to press them into the perfusion ring again.

FIGS. 5a and 5b are corresponding sectional views showing the operation of the embodiment shown in FIGS. 3 and 1a2. An alternating vertical liquid flow in pipette tip c is created by moving the plunger (not shown) of the liquid conveying device, and the liquid flow is passed through the annular receiving portion into the inner volume of the perfusion ring a. The inner volume (liquid j and objects i) is separated from the outer liquid bath 1 by pressing the ring. The liquid flow from the pipette tip c is deflected laterally according to the bent double-headed arrows inside the ring, with the liquid level k fluctuating inside the ring a.

According to FIG. 5b, the dimension of the ring a is increased in order to cover the whole tip c of the pipette. The perfusion ring forms a large volume cup which simultaneously carries the tip c and improves the stability of the arrangement. The ring (receiving portion) and the tip can be in locked engagement.

The apparatuses of the invention are suited in a particularly advantageous manner for implementing the following methods for treating objects in liquid baths. However, there are also advantages for the treatment steps proper (see below), as are described in DE-OS-43 21 061. The treatment steps described in said publication are herewith explicitly included in the description of the present invention and are part of the subject matter of the patent application.

In a treatment method of the invention for the manipulation of perfusion rings, a tip-like inlet member of a liquid conveying device is inserted in a non-positive manner into a holding member of a perfusion ring, and the perfusion ring is moved with the help of the inlet member to the place of treatment. The non-positive connection between the inlet member and the perfusion ring is designed such that the perfusion ring can be transported in a reliable manner and can be pressed against the bottom of the liquid bath for forming a tight contact surface relative to the bottom of the liquid bath with the help of the inlet member of the liquid conveying device. After the treatment operation the perfusion ring is again moved with the help of the inlet member to a stripping device on which the perfusion ring is moved to a storing device. The said manipulation steps can be performed either manually by an operator or automatically with the help of a manipulator system which is described with reference to FIG. 6 with the help of an example regarding a ring with inlet member (pipette tip).

The manipulator system 60 according to FIG. 6 comprises a preparation station 61, at least one treatment station 62 and a storing station 63. The liquid conveying device 64 is movable with the help of a manipulator 65 between the stations. The manipulator 65 is operated by an x-y-z control unit (not shown). The control unit preferably contains an image processing system which receives input signals from a picture recording device 66 (e.g. video or CCD camera) or a microscope 69. The preparation station 61 contains a pipette tip supplier 610, a reservoir 611 for treating liquids and a perfusion ring supplier 612. The at least one treatment station 62 contains at least one liquid bath in accordance with the above explanations. Furthermore, the treatment station 62 contains a base holding device which carries additional means (not shown) for supplying the liquid bath 1, for heating and the like, and possibly a further bath 11, and at least one container for receiving the liquid bath 1. The storing station 63 comprises a liquid collector 631 and a stripping device 632 for perfusion rings. The liquid conveying device is e.g. composed of a pipette tip 641 and a proportioning device 642.

In a first step of the method, the liquid conveying device 64 is moved to the preparation station 61 for receiving the pipette tip 641, which acts as an inlet member, at 610 and is fed with a treatment liquid at reservoir 611. Before or after the feeding operation, the perfusion ring is received by moving or piercing the pipette tip 641 into a perfusion ring according to one of the above-explained embodiments. Feeding with a treatment liquid and reception of the perfusion ring can be carried out in a fully automatic manner according to the invention by using a suitable sensor technique (in particular the picture recording device 66). Depending on the constructional shape of the ring, these operations may be followed by a step in which an attachment cap T of a suitable size is received. Subsequently, the treatment steps (see below) are performed and after the treatment has been concluded, the liquid conveying device 64 is emptied at the storing station 63 into the liquid collector 631 and the perfusion ring and/or the pipette tip 641 is/are stored by mechanical removal with the aid of the stripping device 632.

In the case of perfusion rings having wall chambers (see FIGS. 1, a9, a10) a pipette need not be received. The perfusion rings are directly attached to the liquid conveying device. In such a case the ring (e.g. a10) is first received and fed with treatment liquid at 611.

The stripping device 632 is configured to strip off the pipette tip 641 and the perfusion ring a from the liquid conveying device 64 either at the same time or successively. To this end, the stripping device 632 has corresponding mechanical gripping device, such as a suitably shaped fork construction into which the pipette tip 641 and/or the perfusion ring a can be introduced and removed through a corresponding vertical movement of the pipette tip 641.

The treatment steps comprise recording pictures or images of the objects i in the liquid bath 1 with the help of the picture recording device 66. In an analyzing step, parameters of the objects i are determined, for instance the total number of objects, the number of objects adhering to the surface, the formation of object clusters, or the like, possibly in response to the temperature of the liquid bath 1. At the same time the coordinates of the objects are stored for controlling the manipulator 65.

According to a preferred embodiment, the pictures are subjected to an image recognition and/or image processing method. This image recognition/processing is adapted to identify predetermined clones or cell aggregates. The image recognition/processing is implemented on the basis of any common procedure being known as such. In response to the identification of certain objects, the further treatment can be controlled in a predetermined manner.

Following the manipulation steps (receiving the pipette tip 641, feeding with the treatment liquid and receiving a perfusion ring a), the perfusion ring a is sealingly placed on the surface e and at least one of the following treatment steps is performed. The treatment may comprise introducing the treatment liquid for a specific period of time into the treatment portion defined by the perfusion ring a, forming a directed liquid flow (possibly with alternating flow directions) in the treatment area or drawing the objects i into the liquid conveying device. It is also possible that drawn objects are moved by the liquid conveying device 64 from the liquid bath 1 into at least one further liquid bath (not shown) to perform further perfusion steps in said bath. The generation of a reciprocating fluid flow in the treatment area serves, in particular, local flushing, incubation, removal, mixing, perfusion, dilution, isolation and/or removal of objects. The treatment allows the defined perfusion of a cell culture on a substrate followed by a counting step for a quantitative analysis of the culture.

The right part of FIG. 6 schematically shows a control unit 67 with a display device 68 which displays thereon an image of the objects i to be treated (e.g. cells). A method of the invention comprises the reproducible removal of a specific number of objects and the transfer into another liquid bath for reducing the object density or, at the beginning of new growth, in a new volume. Such a procedure can be implemented according to the invention in a particularly advantageous manner because the perfusion rings of the invention have an inner volume that can be standardized.

By analogy, the steps explained with reference to the automated system according to FIG. 6 can also be carried out manually. Combinations between manual and automated processing operations are also possible if, e.g., in the case of biological applications specific cell clusters with particular characteristics have been determined through special fluorescence or growth properties or other marks, and these are marked with an image processing system, for instance on a screen, with the help of a cursor. Following the determination of the coordinates by the system, the pipette tip is moved with the perfusion ring to the cell cluster (cell clones) determined so as to separate the cluster from the remaining cells. It is also possible to remove cells repeatedly from the surface of a cell dish to carry out diluting steps in a predetermined manner.

Perfusion rings of the invention have the advantage of a considerably simplified structure. They can, in particular, be made in one production step (e.g. injection molding, pressing or the like). Moreover, a combination with a liquid supply device is considerably simplified because no additional connection pieces are required. A perfusion operation can immediately be carried out in the ring which is directly attached to the liquid conveying device. The perfusion rings can be combined with any desired types of pipettes (conventional air displacement pipettes, special pipettes such as the so-called Eppendorf pipettes or Gilson pipettes, or the like). The pipette tip which is connected to a perfusion ring (see FIG. 3, right part) is attachable to any desired pipette ends or needles, or the like, in the manner of an adapter.

Systems of the invention are also suited for rapidly mixing liquids. There are applications in the screening of chemical reactions. When a volume comprising a solution A is received in a pipette (or the wall of the perfusion cup, FIGS. 1, *a*9, *a*10), and the ring device is sealingly mounted on a surface in a volume comprising reaction liquid B, the two liquids can be rapidly mixed by emptying the solution A into the perfusion cup. With the help of optical evaluation methods, for instance observing a color reaction or also methods, such as spectral analysis, etc.), reaction components can be selected. The reaction mixture contained in the cup is then removed entirely and emptied, and the cycle can start again. The reaction components can be separated from one another via an air cushion by drawing air into the nozzle-like channel at the bottom side of the perfusion cup.

While the invention has been described with reference to specific embodiments, other embodiments can be readily envisioned by those of ordinary skill in the art. Accordingly, modifications, substitutions, changes and/or omissions may be made without departing from the spirit and scope of the invention defined in the appended claims.

What is claimed is:

1. A device for treating objects within a defined treatment area of a liquid bath, comprising:
    a ring having a wall portion, a lower edge portion, an upper edge portion and an interior space, said lower edge portion being capable of being sealingly positioned on the bottom of said liquid bath to form said defined treatment area;
    a holding member connected to said upper edge portion and in communication with said interior space, said holding member being capable of engaging a tip-like inlet member of a liquid conveying device in a non-positive, detachable manner;
    wherein a liquid in said liquid conveying device can be discharged into said defined treatment area of said liquid bath when said liquid conveying device is engaged with said holding member, said defined treatment area being formed in said interior space of said ring by sealingly positioning said lower edge portion on said bottom of said liquid bath,
    wherein said wall portion comprises a soft elastic material and wherein said holding member is formed by sealingly piercing said wall with said inlet member.

2. The device according to claim 1, wherein said holding member projects in the direction of said interior space through said wall portion.

3. The device according to claim 2, wherein said wall portion has a thick area through which said holding member projects at an angle of no greater than 90 degrees to said lower edge portion.

4. The device according to claim 3, wherein said holding member has an inner stop to limit the engagement between said inlet member and said holding member.

5. The device according to claim 1, wherein said lower edge portion is notched such that said notches are closed in a liquid-tight seal when said lower edge portion is sealingly positioned on said bottom of said liquid bath.

6. The device according to claim 1, wherein said lower edge portion comprises a soft elastic coating.

7. The device according to claim 1, wherein said lower edge portion is capable of sealingly engaging an attachment cap, said attachment cap being capable of being sealingly mounted on said bottom of said liquid bath thereby forming said defined treatment area.

8. A device for treating objects within a defined treatment area of a liquid bath, comprising:
    a ring having a lower edge portion, an upper edge portion, an interior space and a wall portion with an interior chamber in communication with said interior space, said lower edge portion being capable of being sealingly positioned on the bottom of said liquid bath to form said defined treatment area;
    a holding member positioned on said upper edge portion and in communication with said interior chamber, said holding member being capable of engaging a tip-like inlet member of a liquid conveying device in a non-positive, detachable manner;
    wherein a liquid in said liquid conveying device can be discharged into said defined treatment area through said interior chamber when said inlet member is engaged with said holding member, said defined treatment area being formed in said interior space of said ring by sealingly positioning said lower edge portion on said bottom of said liquid bath,
    wherein said lower edge portion comprises a soft elastic coating.

9. The device according to claim 8, wherein said ring comprises a soft elastic material.

10. The device according to claim 8, wherein said lower edge portion is capable of sealingly engaging an attachment cap, said attachment cap being capable of being sealingly mounted on said bottom of said liquid bath thereby forming said defined treatment area.

11. The device according to claim 8, wherein said interior space of said ring is divided by a partition wall into a perfusion volume space and a receiving space capable of accommodating an optical observation device.

12. The device according to claim 11, wherein said wall portion has at least two interior chambers, and at least one of said interior chambers is in communication with said perfusion volume space.

13. A mounting ring for a pipette having a tip-like end portion, comprising a ring surrounding said tip-like end portion and having a wall portion, a lower edge portion, an upper edge portion and an interior space, said lower edge portion facing away from said tip-like end portion and being capable of being sealingly positioned on the bottom of said liquid bath to form said defined treatment area, said ring having a holding member being positioned in said interior space of said ring and connected to said upper edge portion, said holding member being fixed to said tip-like end portion;

wherein a liquid in said pipette can be discharged into said defined treatment area of said liquid bath, said defined treatment area being formed in said interior space of said ring by sealingly positioning said lower edge portion on said bottom of said liquid bath.

14. A perfusion apparatus comprising a preparation station, a treatment station having one or more liquid baths, a storing station, at least one liquid conveying device capable of treating biological objects in at least one liquid bath of said treatment station, a picture recording device, and a control device, wherein the device according to claim 1 is used in said treatment station.

15. The perfusion apparatus according to claim 14, wherein the mounting ring according to claim 13 is used in said preparation station.

16. A method for treating objects within a defined treatment area of a liquid bath with a perfusing liquid flow conveyed by a liquid conveying device having an end portion from which liquid is conveyed, the steps of which comprise:

positioning an object treating device sealingly on said liquid bath to form said defined treatment area, said object treating device comprising a ring having a wall portion made of a soft elastic material, a lower edge portion, an upper edge portion and an interior space, said lower edge portion being capable of being sealingly positioned on the bottom of said liquid bath to form said defined treatment area, and a holding member connected to said upper edge portion and in communication with said interior space, said holding member being capable of engaging said end portion of said liquid conveying device in a non-positive, detachable manner;

engaging said end portion of said liquid conveying device with said holding member by sealingly piercing said wall with said end portion, said liquid conveying device containing a perfusion liquid; and discharging said perfusion liquid from said liquid conveying device into said defined treatment area.

17. The method according to claim 16, wherein said positioning step is accomplished by pressing the device according to claim 1 onto said liquid bath with said engaged liquid conveying device, wherein a liquid-tight seal is formed between said device according to claim 1 and said liquid bath.

18. The method according to claim 16, wherein said positioning step is accomplished through the use of a manipulator connected to and image processing device and a control device capable of receiving positioning coordinates and accordingly controlling the manipulator.

19. The method according to claim 18, wherein said liquid bath contains objects, and further comprising the steps of drawing at least some of said objects are into said liquid conveying device by using said manipulator, then transferring said drawn objects into another liquid bath by using said manipulator.

20. A method for treating objects within a defined treatment area of a liquid bath with a perfusing liquid flow conveyed by a liquid conveying device having an end portion from which liquid is conveyed, the steps of which comprise:

positioning an object treating device sealingly on said liquid bath to form said defined treatment area, said object treating device comprising a ring having a wall portion, a lower edge portion with a soft elastic coating, an upper edge portion and an interior space, said lower edge portion being capable of being sealingly positioned on the bottom of said liquid bath to form said defined treatment area, and a holding member being positioned on said upper edge portion and in communication with said interior space, said holding member being capable of engaging said end portion of said liquid conveying device in a non-positive, detachable manner;

engaging said end portion of said liquid conveying device with said holding member, said liquid conveying device containing a perfusion liquid; and discharging said perfusion liquid from said conveying device into said defined treatment area.

21. The method according to claim 20, wherein said positioning step is accomplished by pressing the device according to claim 8 onto said liquid bath with said engaged liquid conveying device, wherein a liquid-tight seal is formed between said device according to claim 8 and said liquid bath.

22. The method according to claim 20, wherein said positioning step is accomplished through the use of a manipulator connected to and image processing device and a control device capable of receiving positioning coordinates and accordingly controlling the manipulator.

23. The method according to claim 20, wherein said liquid bath contains objects, and further comprising the steps of drawing at least some of said objects are into said liquid conveying device by using said manipulator, then transferring said drawn objects into another liquid bath by using said manipulator.

24. A method for treating objects within a defined treatment area of a liquid bath with a perfusing liquid flow conveyed by a liquid conveying device having an end portion from which liquid is conveyed, the steps of which comprise:

positioning an object treating device sealingly on said liquid bath to form said defined treatment area, said object treating device comprising a ring having a wall portion, a lower edge portion with a soft elastic coating, an upper edge portion and an interior space, said lower edge portion being capable of being sealingly positioned on the bottom of said liquid bath to form said defined treatment area, and a holding member being positioned in said interior chamber of said ring, said holding member being capable of engaging said end portion of said liquid conveying device in a non-positive, detachable manner;

engaging said end portion of said liquid conveying device with said holding member, said liquid conveying device containing a perfusion liquid; and discharging said perfusion liquid from said liquid conveying device into said defined treatment area.

25. A device for treating objects within a defined treatment area of a liquid bath, comprising:

a ring having a wall portion, a lower edge portion, an upper edge portion and an interior space, said lower edge portion being capable of being sealingly positioned on the bottom of said liquid bath to form said defined treatment area;

a holding member connected to said upper edge portion and in communication with said interior space, said holding member being capable of engaging a tip-like inlet member of a liquid conveying device in a non-positive, detachable manner;

wherein a liquid in said liquid conveying device can be discharged into said defined treatment area of said liquid bath when said liquid conveying device is engaged with said holding member, said defined treatment area being formed in said interior space of said ring by sealingly positioning said lower edge portion on said bottom of said liquid bath, wherein said holding member is positioned in said interior space of said ring.

26. The device according to claim 25, wherein said wall portion comprises a soft elastic material and said holding member is an annular receiving portion made of a non-elastic material positioned in the radial center of said interior space through said wall portion.

27. The device according to claim 8, wherein said wall portion comprises a soft elastic material and said holding member is an annular receiving portion made of a non-elastic material positioned in the radial center of said interior space through said wall portion.

28. The device according to claim 25, wherein said holding member is positioned in the radial center of said interior space and is connected to said ring by connection members.

* * * * *